United States Patent [19]

Varney et al.

[11] Patent Number: 5,545,744

[45] Date of Patent: Aug. 13, 1996

[54] CYANO NAPHTHALENE COMPOUNDS

[75] Inventors: Michael D. Varney, Carlsbad; Cindy L. Palmer, La Mesa; Judy G. Deal, Temecula, all of Calif.

[73] Assignee: Agouron Pharmaceuticals, Inc., La Jolla, Calif.

[21] Appl. No.: 450,801

[22] Filed: May 25, 1995

Related U.S. Application Data

[62] Division of Ser. No. 276,929, Jul. 19, 1994, Pat. No. 5,498,727.

[51] Int. Cl.$^6$ .................................. C07C 255/52
[52] U.S. Cl. .............. 558/418; 558/423; 544/159; 544/224; 546/330; 546/339; 548/469; 548/503
[58] Field of Search .................... 558/418, 423; 546/330, 339; 544/224, 159; 548/469, 503

[56] References Cited

U.S. PATENT DOCUMENTS

| | | | |
|---|---|---|---|
| 3,004,975 | 10/1961 | Grob et al. | 260/285.5 |
| 3,853,911 | 12/1974 | Schefczik | 260/326.3 |
| 4,261,896 | 4/1981 | Tomcufcik et al. | 546/200 X |
| 4,369,188 | 1/1983 | Sestanj | 548/437 |
| 4,683,313 | 7/1987 | Laguzza et al. | 548/437 |
| 5,026,869 | 6/1991 | Flaugh | 548/436 |
| 5,039,820 | 8/1991 | Kress et al. | 548/436 |
| 5,079,247 | 1/1992 | Tomcufcik et al. | 514/232.8 |
| 5,362,747 | 11/1994 | Cowart et al. | 514/448 |

FOREIGN PATENT DOCUMENTS 229221 1/1959 Australia.
392768 10/1990 European Pat. Off..
791804 3/1958 United Kingdom.

OTHER PUBLICATIONS

Bowman et al., "1, 3, 4, 5–Tetrahydrobenz [cd] indoles and Related Compounds. Part III.," J. C. S. Perkin I: 438–442 (1973).

Chemical Abstracts, vol. 116, abstract No. 116:128566v, Mar. 30, 1992.

Primary Examiner—Jacqueline Haley
Attorney, Agent, or Firm—Finnegan, Henderson, Farabow, Garrett & Dunner, L.L.P.

[57] ABSTRACT

The invention relates to a process for preparing a substituted 2-amino-benz[cd]indole of the Formula I:

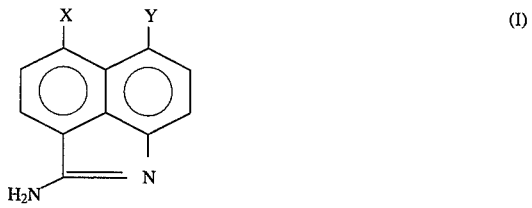

The nitro group of a substituted 1-nitro-8-cyano-naphthalene compound is reduced to an amine group to form a substituted 1-amino-8-cyano-naphthalene compound, which is cyclized to form the substituted 2-amino-benz[cd]indole. The reduction and cyclization may be effected in a one-pot procedure using a reducing agent such as stannous chloride, which generates an acid that cyclizes the reduction product. The syntheses of the 1-nitro-8-cyano-naphthalene compound and its precursors are also described.

3 Claims, No Drawings

CYANO NAPHTHALENE COMPOUNDS

This is a divisional application of Ser. No. 08/276,929 filed Jul. 19, 1994 now U.S. Pat. No. 5,493,727.

FIELD OF THE INVENTION

The invention relates to a process for preparing tricyclic compounds having, as a basic structural unit, the benz[cd]indole ring. More particularly, the invention relates to the preparation of substituted 2-amino-benz[cd]indole compounds. The invention also relates to substituted 1-nitro-8-cyano-naphthalene compounds useful for making the substituted 2-amino-benz[cd]indole compounds, and the preparation of such naphthalene compounds.

The substituted 2-amino-benz[cd]indole compounds made according to the invention are active inhibitors of the enzyme thymidylate synthase (TS). Due to their TS-inhibitory activity, the substituted 2-amino-benz[cd]indole compounds are useful as inhibitors of the growth or proliferation of cells of higher organisms and microorganisms such as yeast and fungi, and as antitumor agents.

BACKGROUND OF THE INVENTION

U.S. Pat. No. 5,079,247 to Tomcufcik et al. describes a process for preparing certain substituted benz[cd]indol-2-(1H)-imines starting from a compound having a preformed benz[cd]indol-2-(1H)-one ring structure with an unsubstituted amino group and a carboxyl group. The starting material is treated with an alkyl halide to obtain a 1-substituted benz[cd]indol-2-(1H)-one, and then reacted with phosphorus pentasulfide to convert the oxygen atom of the carboxyl group to a sulfur atom, giving a 1-substituted benz[cd]indol-2-(1H)-thione. The sulfur atom is then displaced with an amine compound, forming the substituted benz[cd]indol-2-(1H)-imine.

Similarly, U.S. Pat. No. 4,261,896 to Tomcufcik et al. discloses a process where a substituted benz[cd]indole-2-(1H)-one is treated with an alkyl halide to give a 1-substituted benz[cd]indole-2-(1H)-one, which is treated with phosphorus pentasulfide to give a 1-substituted benz[cd]indol-2-(1H)-thione, which in turn is treated with an amine compound to give the substituted benz[cd]indol-2-(1H)-imine. In both of the above processes of Tomcufcik et al., a compound having a fully formed tricyclic nucleus is used as the starting material.

Other processes for preparing various compounds from certain preformed tricyclic ring systems are also known. For example, U.S. Pat. No. 3,853,911 to Schefczik and U.S. Pat. No. 5,039,820 to Kress et al. disclose processes where tricyclic compounds are alkylated. U.S. Pat. No. 3,004,975 to Grob et al. and Australian Patent No. 229,221 describe the manufacture of hydrogenated benz[cd]indoles from 2-oxo compounds, such as 8-amino-1,2,3,4-tetrahydro-naphthalene-1-carboxylic acid lactams. U.S. Pat. No. 4,683,313 to Laguzza et al., U.S. Pat. No. 4,369,188 to Sestanj, British Patent Publication No. 791,804, European Patent Publication No. 0 392 768 A1, and Bowman et al., "1,3,4,5-Tetrahydrobenz[cd]indoles and Related Compounds. Part III," J. C. S. Perkin I, 1973, 438–442, pertain to processes of making benz[cd]indole compounds from a tricyclic material.

U.S. Pat. No. 5,026,869 to Flaugh also discloses two reaction schemes for preparing certain benz[cd]indole compounds, namely 6-substituted-4-dialkylaminotetrahydrobenz[cd]indoles. One reaction scheme, like those described above, starts with a tricyclic compound. A second reaction scheme goes through a tricyclic intermediate, which is prepared from a bicyclic starting material having a 5-membered ring and a 6-membered ring.

Such known processes suffer from various drawbacks and disadvantages, however, such as the requirement of a preformed tricyclic lactam ring or the use of inconvenient starting materials or reaction schemes.

SUMMARY OF THE INVENTION

An object of the invention is therefore to provide a process for forming benz[cd]indole compounds that does not require starting with a tricyclic compound or first forming a lactam ring.

Additionally, an object of the invention is to provide a process for preparing substituted naphthalene compounds that can be converted to substituted 2-amino-benz[cd]indole compounds.

Another object of this invention is to provide a process for preparing substituted 2-amino-benz[cd]indole compounds from naphthalene compounds having substituents prone to react.

An additional object of the invention is to provide a process for making substituted 2-amino-benz[cd]indole compounds in an efficient manner.

A further object of the invention is to attain the convenient preparation of substituted 2-amino-benz[cd]indole compounds that are effective TS inhibitors.

Other objects and advantages of the invention will be apparent from the detailed description below.

The invention generally relates to a process for preparing a substituted 2-amino-benz[cd]indole compound, such as a 6-substituted 2-amino-benz[cd]indole optionally having another substituent at the 5-position. More particularly, the invention relates to the preparation of a 2-amino-benz[cd]indole compound of the Formula I:

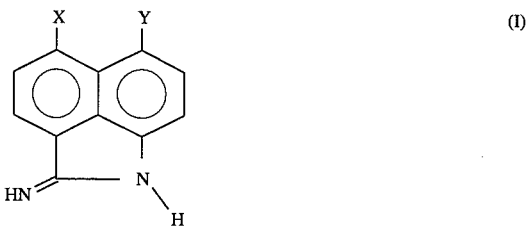

(I)

where X is a hydrogen atom, a halogen atom (Br, Cl, I or F), an alkyl group or a thioether, and Y is an amine group, a thioether group or an alkyl group. Preferably, X is a hydrogen atom or a methyl group, and Y is a tertiary amine group.

The process of the invention may be used to prepare compounds of the Formula I in the various isomeric forms, including tautomers. Thus, where structural formulae are provided, they are intended to include the various isomeric forms of the compounds represented by the formulae.

The process of the invention comprises reacting a nitro compound of the Formula B:

(B)

where X and Y are as defined above, with a reducing agent, and subjecting the reduction product to acidic conditions to form the 2-amino-benz[cd]indole compound. The invention also relates to compounds of the Formula B.

The invention also generally relates to a process for preparing a 2-amino-benz[cd]indole of the above Formula I, comprising: reducing a nitro compound of the Formula B; and cyclizing the resulting reduction product to form the 2-amino-benz[cd]indole compound of the Formula I.

The invention further relates to a process for preparing a benz[cd]indole compound of the Formula I above, where: X is hydrogen or a $C_{1-6}$ alkyl; and Y is a group of the formula

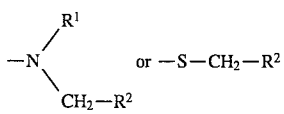

where $R^1$ is hydrogen or an unsubstituted or substituted $C_{1-6}$ alkyl having from 0 to 3 carbon atoms replaced with a hetero atom, and $R^2$ is an aryl or heteroaryl group that is unsubstituted or substituted with an electron-donating or electron-withdrawing moiety. This process comprises (a) reacting an amine compound of the formula

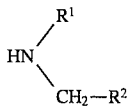

or a thiol compound of the formula $HS-CH_2-R^2$ with a naphthalene compound of the Formula A:

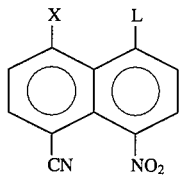

where L is a leaving group such as a halogen atom to form a product of the Formula (A'):

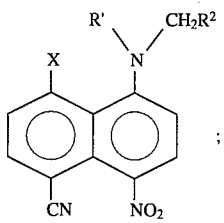

(b) reducing the product of the Formula (A'); and (c) subjecting the product of the reducing (b) to acidic conditions to form the benz[cd]indole compound.

In one embodiment, cyclization is performed as a separate step after reduction. In an alternative embodiment, the reduction advantageously takes place under acidic conditions so that it and cyclization occur together in the same reaction vessel.

The reduction is advantageously performed using a reducing agent that is capable of selectively reducing an aromatic nitro group in the presence of an aromatic cyano group. The reducing is preferably carried out using a reducing agent that generates an acid that cyclizes the reduction product to form the 2-amino-benz[cd]indole. Preferred reducing agents are hydrogen and zinc, iron and tin reagents. Preferably, stannous chloride is used as the reducing agent to generate an acid that cyclizes the reduction product to form the benz[cd]indole compound.

DETAILED DESCRIPTION AND PREFERRED EMBODIMENTS

According to the invention, the nitro group of a 1-nitro-8-cyano-naphthalene compound is reduced to an amine group to form a 1-amino-8-cyano-naphthalene compound, which is treated with acid or cyclized to form a 2-amino-benz[cd]indole compound of the Formula I.

The reduction, which converts the nitro group to an amine group, may be carried out using a suitable reducing agent and reducing conditions. A suitable reducing agent is one that is selective in reducing a nitro group in the presence of a cyano group. Suitable reducing agents include Zn, Fe or Sn reagents, hydrazine compounds, and hydrogen gas ($H_2$) under a vapor pressure of at least one atmosphere (1033.3 g/cm$^2$). A reduction catalyst such as Raney nickel, palladium on charcoal, or palladium on barium sulfate is preferably used when the reducing agent is hydrogen.

In preferred embodiments, the reducing agent is a zinc, iron or tin reagent, i.e., a reagent containing Zn, Fe or Sn in elemental form or containing Zn, Fe or Sn in the form of a salt or another type of compound. Exemplary zinc, iron or tin reagents are zinc metal in acetic acid, iron dust in acetic acid, iron dodecacarbonyl, iron sulfate, tin metal in hydrochloric acid, and tin (II) chloride dihydrate (i.e., $SnCl_2.2H_2O$, stannous chloride). Preferably, the reducing agent is a tin reagent, more preferably stannous chloride.

Preferably, the reduction takes place in the presence of a solvent. Suitable solvents for the reducing reaction are generally polar in nature. Examples of solvents for the reduction reaction include water and organic solvents such as ethanol, methanol, ethyl acetate, tetrahydrofuran, dioxane and acetic acid, and mixtures thereof. Ethanol and methanol are particularly preferred solvents.

The temperature during the reduction is preferably in the range of from about 0° C. to about 200° C., more preferably from about 25° C. to about 80° C. The time required for the reduction reaction will depend to a large extent on the temperature used and the relative reactivity of the intermediate compound, and is preferably from about 10 minutes to about 2 hours. More preferably, the reaction time is from about 30 minutes to about an hour.

The reduced compound having an amino group formed in the reduction reaction may be isolated and subsequently used in a separate cyclizing step. Alternatively, the reduction product may be used directly in the cyclization reaction without isolation or further treatment. In either case, the cyclization is carried out to form a compound of the Formula I by subjecting the 1-amino-8-cyano-naphthalene compound to acidic conditions.

The cyclization takes place at a pH below 7, preferably at a pH of from about 1 to about 4. Preferably, the temperature during cyclization is from about −20° C. to about 100° C., more preferably from about 0° C. to about 40° C. A suitable time for the cyclization reaction is selected taking into account the temperature, the acid employed, and the pH of the reaction medium. Preferred cyclization times are from about ten minutes to about twenty-four hours, more preferably about one hour.

When carrying out the reduction and cyclization reactions as sequential steps, preferably similar reaction conditions are employed in both steps. In the alternative embodiment where the reducing is carried out under acidic conditions to allow cyclization to occur spontaneously as the reduced compound containing an amino group becomes available, reduction and cyclization take place under the same reaction conditions and in the same solvent system; this single-step embodiment advantageously saves time and effort by eliminating an intermediate recovery and work-up operation.

In carrying out the reducing and cyclizing reactions together, a compound that generates an acid as a by-product of the reduction is used as the reducing agent. Stannous chloride is a preferred reducing agent.

The 1-amino-8-cyano-naphthalene product of the reduction reaction cyclizes spontaneously to form a 2-amino-benz[cd]indole compound in the presence of an inorganic or organic acid. Exemplary acids that may be used to effect the cyclization reaction include hydrochloric acid, hydrobromic acid, acetic acid, tosic acid, methane-sulfonic acid, benzene-sulfonic acid, sulfuric acid and nitric acid, which are generally used in trace amounts.

The 2-amino-benz[cd]indole compound thus produced may be isolated by a suitable method, e.g., by known techniques such as precipitation, extraction with an immiscible liquid, evaporation of solvent, or a combination of these or other appropriate methods. The isolated 2-amino-benz[cd]indole compound may be purified by a suitable purification procedure, e.g., by a known technique such as recrystallization, chromatography, trituration with a nonsolvent or a partial solvent, vacuum distillation, countercurrent extraction or the like.

The 1-nitro-8-cyano-naphthalene compound employed in the reduction reaction may be prepared by reacting a naphthalene compound of the Formula A to replace the leaving group L with the desired substituent Y. Preferably, L is a chlorine or fluorine atom.

In this step where the starting naphthalene compound of the Formula A is reacted, an organic solvent is used, which is preferably selected from dimethylsulfoxide (DMSO), dioxane dimethoxy ethane, tetrahydrofuran (THF), methylene chloride and N,N-dimethylformamide (DMF). A preferred solvent is DMSO.

This step is preferably carried out in the presence of an organic or inorganic neutralizing agent. Suitable neutralizing agents are weak bases. Exemplary inorganic bases are calcium carbonate, sodium carbonate, potassium carbonate and cesium carbonate. Representative organic bases are substituted amines, such as N,N-diisopropylethanolamine (DIEA), trimethylamine, triethylamine, dimethyl-sec-butylamine, N-methyl-N-ethylaniline, N,N-dimethylaniline, diazobicyclicundecine and tributylamine. A preferred neutralizing agent is DIEA.

The reaction of the compound of the Formula A may be carried out at a temperature of from about 25° C. to about 200° C. for a time of about 1 hour to about 24 hours. A preferred reaction temperature is from about 75° C. to about 140° C. A preferred reaction time is about 5–7 hours.

Preferably, the 1-nitro-8-cyano-naphthalene compound of the Formula A is derived from an unsubstituted or substituted 1-nitro- 8-halo-naphthalene precursor that is cyanylated using a cyanylating agent such as cuprous cyanide in a solvent such as N,N-dimethylformamide (DMF). Preferably, the 8-position halogen atom is a bromine, chlorine or iodine atom. Thus, the 1-nitro-8 -cyano-naphthalene compound of the Formula A may be readily prepared in good yield by a process in which an unsubstituted or substituted 1-nitro-8-bromo-naphthalene, 1-nitro-8-chloronaphthalene or 1-nitro-8-iodo-naphthalene compound is reacted with cuprous cyanide to form a 1-nitro-8-cyano-naphthalene precursor of a compound of the Formula A.

Attachment of the substituents on the naphthalene ring may be accomplished by a suitable method for derivatizing the naphthalene ring. Substituents may be attached to the naphthalene ring using a substitution reaction before or after the reduction and cyclization reactions. Where the substitution reaction involves the use of a reactant prone to attack the amine or cyano group, the reduction and cyclization reactions are preferably performed first. On the other hand, where the substituents to be added to the naphthalene ring are prone to react with the indole ring, the substitution reaction is preferably carried out first. In either sequence, reaction at an undesired location may be prevented by first adding a labile protecting group to the site at which reaction is not desired.

Thus, a process as described above may be employed to prepare compounds of the Formula I, where X is a hydrogen atom or an alkyl group and Y is an amine group or a thioether group. Particularly preferred compounds of the Formula I are those wherein: X is hydrogen or a $C_{1-6}$ alkyl; and Y is a substituent of the formula $N(R^1)(CH_2R^2)$ or $SCH_2R^2$ where $R^1$ is hydrogen or a substituted or unsubstituted $C_{1-6}$ alkyl having from 0 to 3 carbon atoms each replaced by a hetero group (e.g., N, S or O), and $R^2$ is an aryl or hetercaryl group that is unsubstituted or substituted with an electron-donating or electron-withdrawing moiety. Of course, the valence shells of the compounds are filled. Thus, when $R^1$ is an alkyl having a nitrogen atom replacing a carbon atom, attached to the nitrogen atom to fill its valence shell may be: two hydrogen atoms; two substituents, such as $C_{1-6}$ alkyls, which are the same or different; or a hydrogen atom and one such substituent.

Representative alkyl groups for X are methyl, ethyl, isopropyl, t-butyl, n-pentyl, 2-methylpentyl and 2-ethylpropyl. Preferably, X is hydrogen or methyl.

Exemplary unsubstituted alkyl groups for $R^1$ are methyl, ethyl, isopropyl, t-butyl, n-pentyl, 2-methylpentyl and 2-ethylpropyl. Representative alkyl substituents are hydroxy, alkoxy, amino, nitro, aryl and aryloxy groups. Exemplary substituted alkyl groups having from 1 to 6 carbon atoms and from 0 to 3 hetero atoms are hydroxyethyl, —$CH_2$—S—$CH_3$ and —$CH_2$—$NH_2$. Preferably, $R^1$ is selected from hydrogen, methyl, ethyl, hydroxyethyl, n-propyl, isopropyl, hydroxypropyl and —$CH_2$—S—$CH_3$. More preferably, $R^1$ is methyl.

Exemplary aromatic or heteroaromatic rings for $R^2$ are furanyl, pyrrolyl, thiophenyl, benzofuranyl, indolyl, benzothiophenyl, isoxazolyl, pyrazolyl, isothiazolyl, pyridazinyl, morpholinyl, phenyl, pyridinyl, quinolinyl, isoquinolinyl, quinazolinyl, naphthyl, diazinyl, triazinyl, anthracenyl, phenanthrenyl, acridinyl and pteridinyl. Preferably, $R^2$ has a phenyl, naphthyl or heteroaromatic ring, more preferably, a phenyl, pyridinyl, pyridazinyl or indolyl ring.

$R^2$ may be unsubstituted or substituted with one or more electron-donating or electron-withdrawing moieties. Representative electron-donating or electron-withdrawing moieties are halo, hydroxy, alkoxy, alkyl, hydroxyalkyl, haloalkyl, cyano, carbalkoxy, carbamyl, carbonyl, carboxy, amino acid carbonyl, amino acid sulfonyl, sulfamyl, sulfanilyl, sulfhydryl, sulfino, sulfinyl, sulfo, sulfonamido, sulfonyl, phenylsulfonyl, phenylmercapto, phosphazo, phosphinico, phosphino, phospho, phosphono, phosphoro, phosphoroso, morpholinosulfonyl, piperazinylsulfonyl and indolylsulfonyl. These moieties may be substituted where appropriate. Preferred electron-donating or electron-withdrawing moieties include —$CF_3$, —$CH_3$, —$SO_2$—$C_6H_5$ and

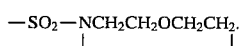

In one particularly preferred embodiment, $R^2$ is an N-substituted indolyl ring. In another particularly preferred embodiment, $R^2$ is a phenyl group para-substituted with an electron-withdrawing moiety, preferably a 4-morpholinosulfonyl or 4-phenylsulfonyl moiety.

EXAMPLES

The examples provided below illustrate various aspects and embodiments of the invention.

In the examples, proton magnetic resonance spectra were determined using a General Electric QE-300 spectrometer operating at a field strength of 300 MHz. Chemical shifts are reported in parts per million (δ); the references were set such that in $CDCl_3$ the $CHCl_3$ peak was at 7.26 ppm, and in DMSO-$D_6$ the DMSO peak was at 2.49 ppm. Standard and peak multiplicities are designated as follows: s—singlet; d—doublet; dd—doublet of doublets; t—triplet; brs—broad singlet; brd—broad doublet; br—broad signal; and m—multiplet.

Mass spectra were determined using a VG 7070E-HF high-resolution mass spectrometer with the direct insertion method, an ionizing voltage of 70eV, and an ion source temperature of 200° C. Infrared (IR) absorption spectra were made on a Perkin-Elmer 457 spectrometer. Elemental microanalysis gave results for the elements stated with an accuracy of ±0.4% of the theoretical values.

N,N-Dimethylformamide (DMF) was dried over activated 3Å molecular sieves. Tetrahydrofuran (THF) was distilled from sodium benzophenone ketyl under nitrogen.

Flash chromatography was performed using Silica Gel 60 (Merck Art 9385). Where the crude solid was insoluble in the chosen eluant, it was dissolved in a more polar solvent, and Merck Art 7734 silica was added. The slurry was evaporated to dryness en a rotary evaporator fitted with a coarse glass frit to prevent spraying of the silica. The coated silica was then applied to the column. Thin layer chromatographs (TLC) were performed on precoated sheets of Silica 60 $F_{254}$ (Merck Art 5719).

Organic extracts were dried over anhydrous $Na_2SO_4$ or anhydrous $MgSO_4$. Melting points (m.p.) (uncorrected) were determined on a Mel-Temp apparatus.

Example 1

N6-Methyl-N6-pyridin-4-ylmethyl-benz[cd]indole-2,6-diamine

The title compound (11) was prepared according to the following reaction scheme:

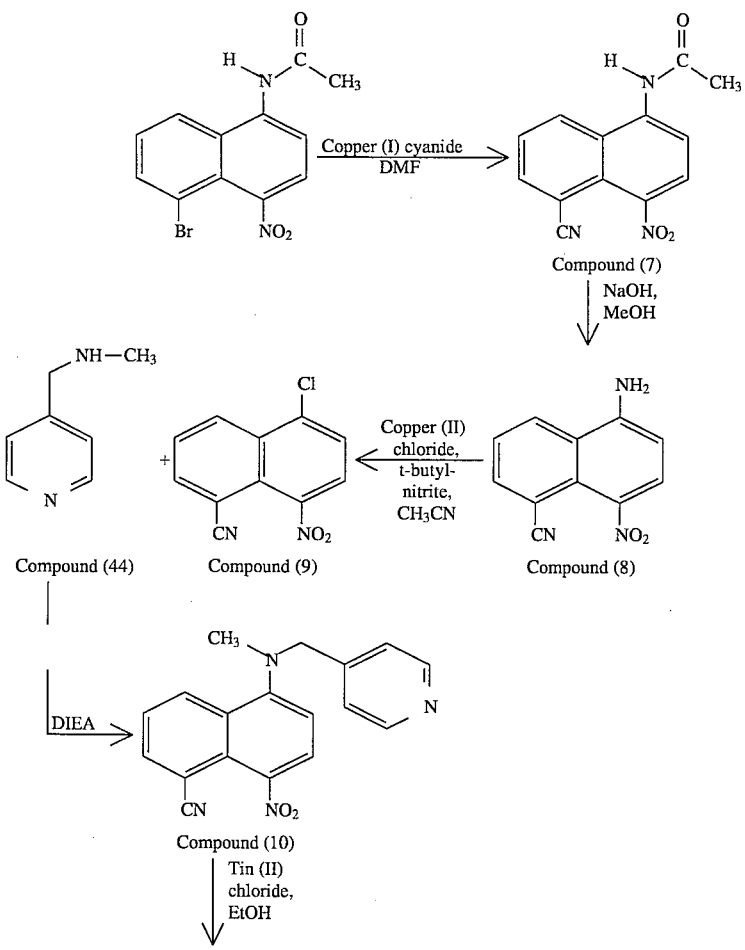

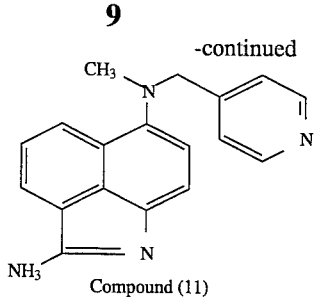

Compound (11)

Preparation of N-(5-Cyano-4-nitro-naphthalen-1-yl)-acetamide:

A stirred solution of 3.83 g (12.39 mmol) of N-(5-bromo-4-nitro-naphthalene-1-yl)-acetamide (K. Fries, Ber. 57, 1924, 501) and 1.28 g (14.29 mmol) of copper (I) cyanide in 40 ml of DMF was heated at reflux for one hour. The cooled reaction mixture was poured into a 30% aqueous ethylenediamine solution and extracted repeatedly with ethyl acetate (EtOAc). The combined organic layers were washed with 10% NaCN solution, washed with saturated NaCl solution, and then dried (anhydrous $Na_2SO_4$), and the solvent was removed under reduced pressure. The resulting wet solid was triturated with diethyl ether ($Et_2O$), filtered and dried (2.15 g). The filtrate was concentrated, and the residue was flash chromatographed on silica, eluting $CH_2Cl_2$:EtOAc (1:1), to give 0.13 g of product. The overall yield of N-(5-cyano-4-nitro-naphthalen-1-yl)-acetamide (7) was 2.28 g (72%) as a yellow solid, m.p. 267°–268° C. (decomp.).

IR (KBr) 3270, 2230, 1670, 1520, 1342, 1270 $cm^{-1}$.

$^1$H NMR (DMSO-$D_6$) δ: 2.24 (s,3H), 7.89 (t,1H,J=8.7Hz), 8.10 (d,1H,J=8.5Hz), 8.30 (d,1H,J=8.5Hz), 8.42 (d,1H,J=7.2Hz), 8.70 (d,1H,J=8.7Hz), 10.50 (brs,1H).

Anal. calc. for $C_{13}H_9N_3O_3 \cdot 0.35H_2O$: C, 59.70; H, 3.74; N, 16.07. Found: C, 59.92; H, 3.62; N, 15.87.

Preparation of 5-Amino-8-nitro-naphthalene-1-carbonitrile:

A solution of 2.34 g (9.18 mmol) of the above compound and 9 ml of 2N sodium hydroxide (NaOH) solution in 50 ml of methanol (MeOH) was heated at reflux for thirty minutes. The reaction mixture was cooled, and the precipitate that formed was collected, washed with water, washed with cold methanol and dried, producing 1.75 g (89% yield) of 5-amino-8-nitro-naphthalene-1-carbonitrile (8) as an orange solid, m.p. 255°–260° C. (decomp.).

IR (KBr) 3495, 3380, 3260, 2220, 1690, 1575, 1525, 1482, 1295 $cm^{-1}$.

$^1$H NMR (DMSO-$D_6$) δ: 6.73 (d,1H,J=8.8Hz), 7.64 (s,2H), 7.68 (t,1H,J=8.5Hz), 8.17 (d,1H,J=8.8Hz), 8.26 (d,1H,J=7.3Hz), 8.61 (d,1H,J=8.5Hz).

Anal. calc. for $C_{11}H_7N_3O_2$: C, 61.97; H, 3.31; N, 19.71. Found: C, 61.74; H, 3.40; N, 19.53.

Preparation of 5-Chloro-8-nitro-naphthalene-1-carbonitrile:

To a partially dissolved solution of 1.35 g (10.04 mmol) of copper (II) chloride and 1.70 ml (12.86 mmol) of tert-butylnitrite in 100 ml of acetonitrile ($CH_3CN$) was added a suspension of 1.79 g (8.40 mmol) of the above aniline compound in 50 ml of acetonitrile. After all of the compound had been added, the reaction was stirred another thirty minutes at room temperature, and was then poured into 0.5N hydrochloric acid and extracted twice with EtOAc. The combined organic layers were washed with saturated NaCl solution and dried over anhydrous $MgSO_4$, and the solvent was removed under reduced pressure. The residue was recrystallized from ethanol (EtOH) to give 1.47 g of 5-chloro-8-nitro-naphthalene-1-carbonitrile (9) as light-brown needles, m.p. 210°–212° C. Another 0.20 g of compound (9) was obtained after flash chromatography of the concentrated mother liquors, eluting hexanes:$CH_2Cl_2$ (1:1). The overall yield was 1.67 g (86%).

IR (KBr) 3100, 2225, 1560, 1530, 1360, 1210, 1050 $cm^{-1}$.

$^1$H NMR (DMSO-$D_6$) δ: 8.02 (t,1H,J=7.4Hz), 8.10 (d,1H,J=8.2Hz), 8.32 (d,1H,J=8.2Hz), 8.53 (d,1H,J=7.3Hz), 8.74 (d,1H,J=8.7Hz).

Anal. calc. for $C_{11}H_{15}ClN_2O_2$: C, 56.79; H, 2.17; Cl, 15.24; N, 12.04. Found: C, 56.87; H, 2.19; Cl, 15.15; N, 12.00.

Preparation of Methyl-pyridin-4-ylmethyl-amine:

A pressure tube was charged with 2.00 g (14.00 mmol) of 4-pyridine-carboxaldehyde and about twenty-five 3Å molecular sieves. After saturating the aldehyde with anhydrous methylamine, the tube was sealed and heated at 100° C. for six hours. The contents of the tube plus a catalyst of 0.23 g of 5% Pd on carbon were placed under an atmosphere of $H_2$ (40 psi) for eighteen hours. The catalyst was removed by filtering through Celite (diatomaceous earth material), and the filtrate was concentrated under reduced pressure. The residue was flash chromatographed on silica, eluting $CH_2Cl_2$:$NH_3$-saturated MeOH (15:1). Consequently, 2.10 g (92% yield) of methyl-pyridin-4-ylmethyl-amine (44) was produced as a colorless liquid.

IR (neat) 3293 (broad), 2797, 1605, 1561, 1416, 1362 $cm^{-1}$.

$^1$H NMR (CDCl$_3$) δ: 2.46 (s,3H), 3.78 (s,2H), 7.26 (d,2H, J=6.2Hz), 8.54 (d,2H,J=5.9Hz).

Anal. calc. for $C_7H_{10}N_2 \cdot 0.15H_2O$: C, 67.33; H, 8.31; N, 22.43. Found: C, 67.16; H, 8.33; N, 22.23.

Preparation of 5-(Methylpyridin-4-ylmethyl-amino)-8-nitro-naphthalene-1-carbonitrile:

A dimethylsulfoxide (DMSO) solution of 0.51 g (2.21 mmol) of chloronaphthalene compound (9), 0.57 g (4.67 mmol) of pyridine compound (44), and 0.80 ml (4.59 mmol) of DIEA was heated at 85° C. for six hours. The reaction mixture was cooled, poured into water, and extracted three times with ethyl acetate. The combined organic layers were dried over anhydrous $MgSO_4$ and the solvent was removed under reduced pressure. The residue was flash chromatographed on silica, eluting $CH_2Cl_2$:EtOAc (1:1). There was obtained 0.26 g (37% yield) of 5-(methylpyridin-4-ylmethyl-amino)-8-nitro-naphthalene-1-carbonitrile (10) as a yellow solid, m.p. 153°–156° C.

IR (KBr) 2222, 1570, 1505, 1518, 1412, 1323, 1304, 1206 $cm^{-1}$.

$^1$H NMR (CDCl$_3$) δ: 2.94 (s,3H), 4.41 (s,2H), 7.15 (d,1H,J=8.4Hz), 7.32 (d,2H,J=6.0Hz), 7.66 (t,1H,J=7.3Hz), 8.03 (d,1H,J=8.4Hz), 8.13 (d,1H,J=7.2Hz), 8.55 (d,1H,J=8.6Hz), 8.64 (d,1H,J=6.0Hz).

Anal. calc. for $C_{18}H_{14}N_4O_2 \cdot 0.50H_2O$: C, 66.04; H, 4.62; N, 17.12. Found: C, 66.04; H, 4.47; N, 17.07.

Preparation of N6-Methyl-N6-pyridin-4-ylmethyl-benz[cd]indole-2,6-diamine:

A stirred solution of 0.21 g (0.66 mmol) of compound (10) and 0.30 g (0.13 mmol) of tin (II) chloride dihydrate in 15 ml of ethanol (EtOH) was heated at 70° C. for forty-five minutes. The reaction mixture was diluted with ethyl acetate and washed with 1N NaOH. The aqueous layer was extracted repeatedly with ethyl acetate until the aqueous layer was nearly colorless. The combined organic layers were dried over anhydrous $MgSO_4$ and the solvent was removed under reduced pressure. The residue was flash chromatographed on silica, eluting $CH_2Cl_2$:$NH_3$-saturated MeOH (9:1). There was obtained 77 mg (41% yield) of amidine compound (11) as an orange solid, m.p. 168°–170° C.

IR (KBr) 3345, 3183, 1665, 1607, 1535, 1462, 1362, 1248 $cm^{-1}$.

$^1$H NMR (CDCl$_3$) δ: 2.86 (s,3H), 4.20 (brs,2H), 4.40 (s,2H), 6.87 (d,1H,J=7.5Hz), 7.05 (d,1H,J=7.5Hz), 7.40 (d,2H,J=5.7Hz), 7.58 (t,1H,J=7.6Hz), 7.79 (d,1H,J=7.0Hz), 8.10 (d,1H,J=8.1Hz), 8.61 (d,2H,J=5.9Hz).

Anal. calc. for $C_{18}H_{16}N_4 \cdot 1.20H_2O$: C, 69.75; H, 5.98; N, 18.07. Found: C, 69.87; H, 6.05; N, 17.97.

Anal. calc. for $C_{18}H_{17}N_4$, M+H: 289.1453. Found: 289.1444.

Example 2

N6-Methyl-N6-pyridazin-4-ylmethyl-benz[cd]indole-2,6-diamine

The title compound (25) was prepared according to the following reaction scheme:

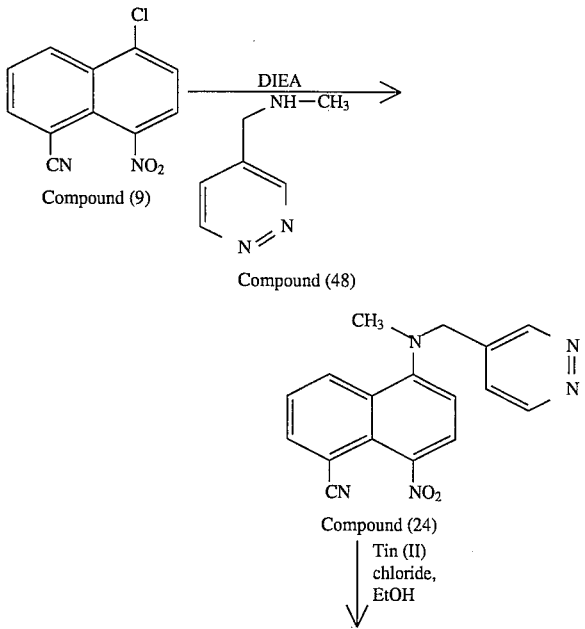

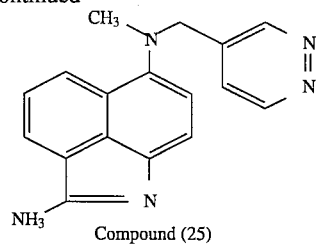

Preparation of Methyl-pyridazin-4-ylmethyl-amine:

Methyl-pyridazin-4-ylmethyl-amine (48) was prepared in a manner analogous to that used to prepare compound (36) described below, except 5-hydroxymethylpyridazine (G. Heinisch, Monat. Chem. 104, 1973, 1354–1359) was used. Compound (48) was isolated (86% yield) as an oil by flash chromatography on silica, eluting $CH_2Cl_2$:$NH_3$-saturated MeOH (9:1).

IR (neat) 3300 (broad), 1661, 1591, 1451, 1379, 1134 $cm^{-1}$.

$^1$H NMR (CDCl$_3$) δ: 2.47 (s,3H), 3.83 (s,2H), 7.49 (d with fine splitting,1H,J=5.2Hz), 9.13 (d with fine splitting,1H, J=5.3Hz), 9.18 (s,1H).

Anal. calc. for $C_6H_9N_3 \cdot 0.50H_2O$: C, 54.52; H, 7.63; N, 31.79. Found: C, 54.74; H, 7.47; N, 31.74.

Preparation of 5-(Methyl-pyridazin-4-ylmethyl-amino)-8-nitro-naphthalene-1-carbonitrile:

5-(Methyl-pyridazin-4-ylmethyl-amino)-8-nitro-naphthalene-1-carbonitrile (24) was prepared in a manner analogous to that described above for the preparation of compound (10), except that compound (9) and pyridazyl amine compound (48) were used as starting materials. Compound (24) (24% yield) was isolated as a yellow foam by flash chromatography on silica, eluting $CH_2Cl_2$:MeOH (25:1).

IR (KBr) 2224, 1572, 1520, 1346, 1235, 1121 $cm^{-1}$.

$^1$H NMR (CDCl$_3$) δ: 2.94 (s,3H), 4.44 (s,2H), 7.21 (d,1H,J=8.3Hz), 7.50 (d with fine splitting,1H,J=5.2Hz), 7.71 (t,1H,J=7.3Hz), 8.02 (d,1H,J=8.3Hz), 8.16 (d,1H,J=7.3Hz), 8.56 (d, 1H, J=7.4Hz), 9.22 (d with fine splitting, 1H,J=5.3Hz), 9.29 (s,1H).

Anal. calc. for $C_{17}H_{13}N_5O_2$, M$^+$: 319.1069. Found: 319.1072.

Preparation of N6-Methyl-N6-pyridazin-r-ylmethyl-benz[cd]indole-2,6-diamine:

Compound (25) was prepared in a manner analogous to that described above for the preparation of compound (11), except cyano-nitro compound (24) was used as the starting material. Compound (25) (23% yield) was isolated as a red-orange solid, m.p. 177°–180° C., by flash chromatography on silica, eluting $CH_2Cl_2$:$NH_3$-saturated MeOH (10:1).

IR (KBr) 3308 (broad), 3067 (broad), 1672, 1537, 1460, 1250 $cm^{-1}$.

$^1$H NMR (CDCl$_3$) δ: 2.88 (s,3H), 3.00–4.00 (brs,2H), 4.42 (s,2H), 6.89 (d,1H,J=7.5Hz), 7.03 (d,1H,J=7.5Hz), 7.55 (d with fine splitting,1H,J=5.2Hz), 7.62 (t,1H,J=7.1Hz), 7.81 (d,1H,J=7.0Hz), 8.09 (d,1H,J=8.2Hz), 9.17 (d with fine splitting,1H,J=5.2Hz), 9.30 (s,1H).

Anal. calc. for $C_{17}H_{15}N_5$: C, 70.57; H, 5.23; N, 24.21. Found: C, 70.43; H, 5.24; N, 24.06.

Anal. calc for $C_{17}H_{15}N_5$, M$^+$: 289.1327. Found: 289.1318.

Example 3

N6-(1-Benzenesulfonyl-1H-indol-4-ylmethyl)-N6-methyl-benz[cd]indole-2,6-diamine

The title compound (34) was prepared according to the following reaction scheme:

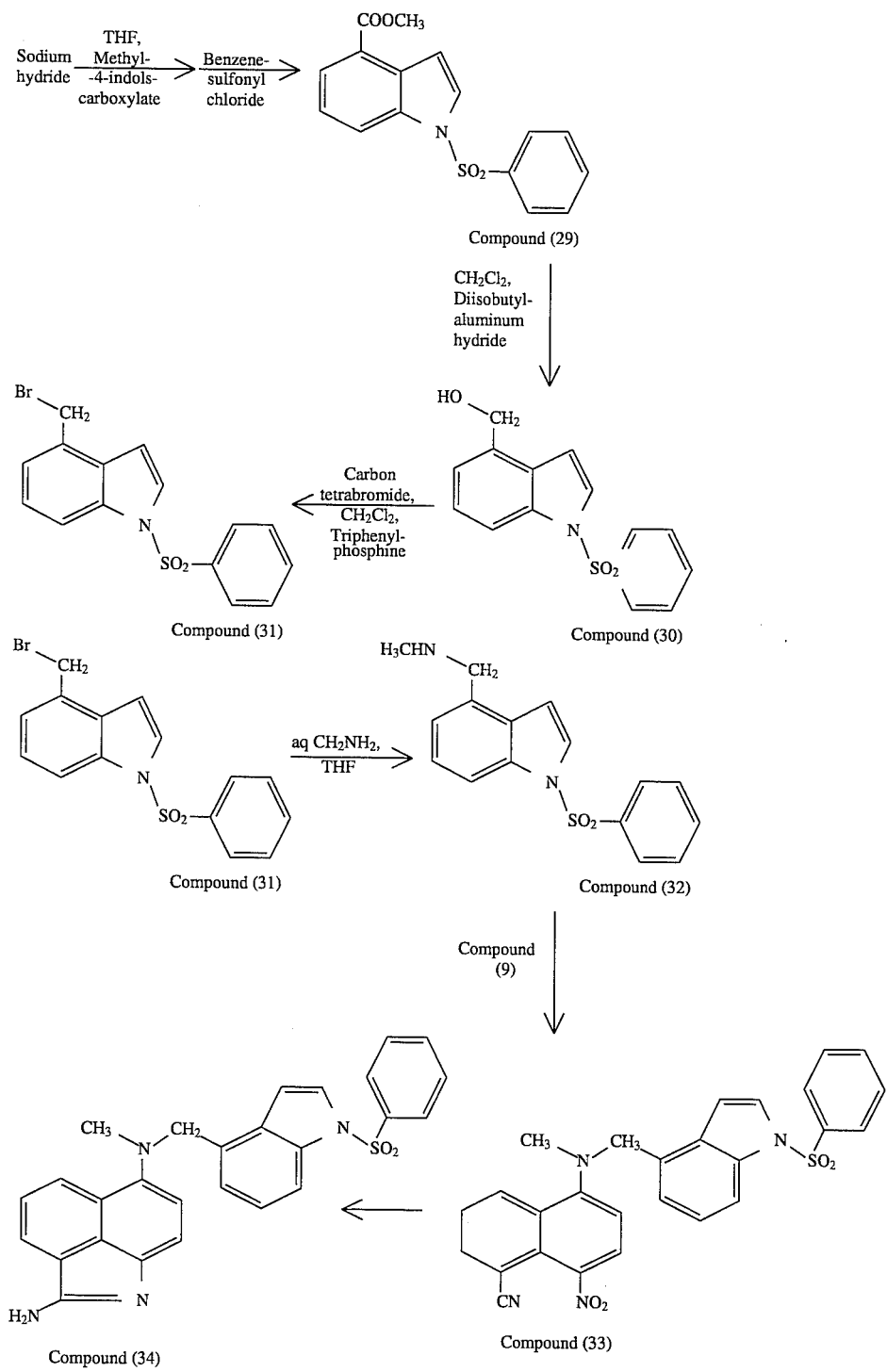

with hexanes, 50 ml of tetrahydrofuran (THF) was added, and the resulting suspension was cooled to 0° C. A solution of 5.31 g (30.31 mmol) of methyl-4-indole-carboxylate in 20 ml of THF was added dropwise. When the addition was complete, the clear yellow solution was stirred for fifteen minutes at 0° C. To this indole-anion was added dropwise Preparation of 1-Benzenesulfonyl-1H-indole-4-carboxylic acid methyl ester:

A flame-dried flask was charged with 1.34 g (34.88 mmol) of sodium hydride (60% dispersion in oil). After washing 4.0 ml (31.34 mmol) of benzenesulfonyl-chloride. After fifteen minutes at 0° C., the reaction mixture was poured into ethyl acetate and washed with saturated NaHCO₃ solution and dried over anhydrous MgSO₄, and the solvent was removed under reduced pressure. The residue was slurried in hot ethanol, cooled and filtered, yielding 7.61 g (80%) of compound (29) as a white solid, m.p. 145°–150° C.

IR (KBr) 3125, 1725, 1450, 1438, 1428, 1372, 1360, 1288, 1275, 1172 cm$^{-1}$.

$^1$H NMR (CDCl$_3$) δ: 3.94 (s,3H), 7.40 (m,5H), 7.70 (d,1H,J=3.7Hz), 7.86 (d,2H,J=8.5Hz), 7.97 (d,1H,J=7.7Hz), 8.21 (d,1H,J=8.3Hz).

Anal. calc. for C$_{16}$H$_{13}$NO$_4$S: C, 60.94; H, 4.16; N, 4.44; S, 10.17. Found: C, 60.86; H, 4.18; N, 4.43; S, 10.10.

Preparation of (1-Benzenesulfonyl-1H-indol-4-yl)-methanol:

To an ice-cold solution of 1.00 g (3.17 mmol) of ester compound (29) in 15 ml of CH$_2$Cl$_2$ was added dropwise 10.20 ml (10.20 mmol) of a 1M solution of diisobutylaluminum hydride in hexanes. After thirty minutes at 0° C., the reaction mixture was poured into 150 ml of saturated Rochelle salt solution and 150 ml of ethyl acetate, and the mixture was stirred vigorously until the layers separated. The aqueous layer was re-extracted with another 150 ml of ethyl acetate. The combined organic layers were similarly washed with saturated Rochelle salt solution and dried over anhydrous MgSO$_4$, and the solvent was removed under reduced pressure. The residue was flash chromatographed on silica, eluting CH$_2$Cl$_2$:EtOAc (20:1). Consequently, there was obtained 0.89 g (98% yield) of (1-benzenesulfonyl-1H-indol-4-yl)-methanol (30) as a white solid, m.p. 89°–91° C.

IR (KBr) 3280 (broad), 1500, 1460, 1370, 1360, 1185, 1165, 1135 cm$^{-1}$.

$^1$H NMR (CDCl$_3$) δ: 1.65 (t,1H,J=5.8Hz), 4.89 (d,2H,J=5.8Hz), 6.83 (d,1H,J=3.7Hz), 7.23 (m,2H), 7.50 (m,3H), 7.61 (d,1H, J=3.7Hz), 7.89 (d,2H,J=7.8Hz), 7.95 (d,1H,J=8.1Hz).

Anal. calc. for C$_{15}$H$_{13}$NO$_3$S: C, 62.70; H, 4.56; N, 4.88; S, 11.16. Found: C, 62.79; H, 4.58; N, 4.92; S, 11.21.

Preparation of 1-Benzenesulfonyl-4-bromomethyl-1H-indole:

To a stirred solution of 0.78 g (2.71 mmol) of alcohol (30) and 1.13 g (3.41 mmol) of carbontetrabromide in 10 ml of CH$_2$Cl$_2$ at 0° C. was added 1.07 g (4.08 mmol) of triphenylphosphine. After one hour at 0° C., the solvent was removed under reduced pressure. The residue was flash chromatographed on silica, eluting CH$_2$Cl$_2$. After trituration with diethyl ether there was obtained 0.82 g (80% yield) of 1-benzenesulfonyl-4-bromomethyl-1H-indole (31) as a white solid, m.p. 127°–128° C.

IR (KBr) 1450, 1428, 1370, 1362, 1285, 1270, 1182, 1129 cm$^{-1}$.

$^1$H NMR (CDCl$_3$) δ: 4.69 (s,2H), 6.85 (d,1H,J=3.8Hz), 7.27 (m,2H), 7.48 (m,2H), 7.55 (m, 1H), 7.66 (d,1H,J=3.7Hz), 7.89 (d,2H,J=7.6Hz), 7.96 (d,1H,J=7.8 Hz).

Anal. calc. for C$_{15}$H$_{12}$BrNO$_2$S: C, 51.44; H, 3.45; Br, 22.82; N, 4.00; S, 9.16. Found: C, 51.53; H, 3.46; Br, 22.89; N, 4.01; S, 9.09.

Preparation of (1-Benzenesulfonyl-1H-indol-4-ylmethyl)-methylamine:

To a stirred solution of 1.0 ml of 40 wt. % aqueous methylamine in 15 ml tetrahydrofuran was added dropwise a solution of 0.72 g (2.06 mmol) of bromide compound (31) in 10 ml of tetrahydrofuran. Thirty minutes after the addition was complete, the volatiles were removed under reduced pressure, and the residue was diluted with ethyl acetate and washed twice with 0.5N HCl. The combined aqueous layers were made basic with 6N NaOH and re-extracted with ethyl acetate. The organic layer was dried over anhydrous MgSO$_4$ and the solvent was removed under reduced pressure. The oily solid that remained was triturated with diethyl ether, giving 0.48 g (77% yield) of (1-benzenesulfonyl-1 H-indol-4-ylmethyl)-methyl-amine (32) as a light-yellow solid, m.p. 75°–77° C.

IR (KBr) 1450, 1360, 1285, 1185, 1170, 1130 cm$^{-1}$.

$^1$H NMR (CDCl$_3$) δ: 2.45 (s,3H), 3.93 (s,2H), 6.80 (d,1H, J=3.7Hz), 7.18 (d,1H,J=7.3Hz), 7.27 (t,1H,J=7.5Hz), 7.50 (m,3H), 7.58 (d,1H,J=3.7Hz), 7.89 (m,3H).

Anal. calc. for C$_{16}$H$_{16}$N$_2$O$_2$S: C, 63.98; H, 5.37; N, 9.33; S, 10.67. Found: C, 63.89; H, 5.40; N, 9.30; S, 10.57.

Preparation of 5-{(1-Benzenesulfonyl-1H-indol-4-ylmethyl)-methyl-amino}-8-nitro-naphthalene-1-carbonitrile:

Compound (33) was prepared in a manner analogous to that used to prepare compound (10) as described above, except that chloronaphthalene compound (9) and amine compound (32) were used as starting materials. The product was subjected to flash chromatography on silica, eluting CH$_2$Cl$_2$, and isolated (40% yield) as a brittle yellow foam, m.p. 95° C. with foaming.

IR (KBr) 2224, 1570, 1520, 1360, 1184, 1132 cm$^{-1}$.

$^1$H NMR (CDCl$_3$) δ: 2.87 (s,3H), 4.59 (s,2H), 6.47 (d,1H, J=3.8Hz), 7.08 (d,1H,J=8.4Hz), 7.31 (m,2H), 7.47 (m,2H), 7.55 (m,2H), 7.58 (m,3H), 7.95 (m,4H), 8.09 (d,1H,J=7.3Hz), 8.52 (d,1H,J=8.6Hz).

Anal. calc. for C$_{27}$H$_{20}$N$_4$O$_4$S.0.50H$_2$O: C, 64.14; H, 4.19; N, 11.08; S, 6.34. Found: C, 63.88; H, 3.83; N, 11.07; S, 6.25.

Preparation of N6-(1-Benzenesulfonyl-1H-indol-4-ylmethyl)-N6-methyl-benz[cd]indole-2,6-diamine:

Compound (34) was prepared in a manner analogous to that used for preparing compound (11), except using cyanonitronaphthalene compound (33) as a starting material. The product was isolated (50% yield) as a red solid, m.p. 116° C. with foaming.

IR (KBr) 3146 (broad), 1641, 1528, 1424, 1371, 1184, 1130 cm$^{-1}$.

$^1$H NMR (CDCl$_3$) δ: 2.60 (brs,2H), 2.81 (s,3H), 4.59 (s,2H), 6.67 (d,1H,J=4.1Hz), 6.85 (d,1H,J=7.6Hz), 7.06 (d,1H, J=7.5Hz), 7.33–7.57 (m,7H), 7.83 (d,1H,J=7.0Hz), 7.89 (m,3H), 8.15 (d,1H,J=8.2Hz).

Anal. calc. for C$_{27}$H$_{22}$N$_4$O$_2$S, M$^+$: 466.1463. Found: 466.1463.

Example 4

N6-Methyl-N6-(2-trifluoromethyl-pyridin-4-ylmethyl)-benz[cd]indole-2,6-diamine

The title compound (38) was prepared according to the following reaction scheme:

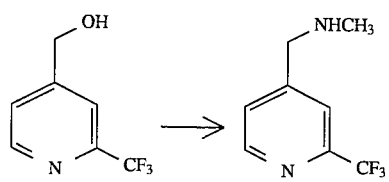
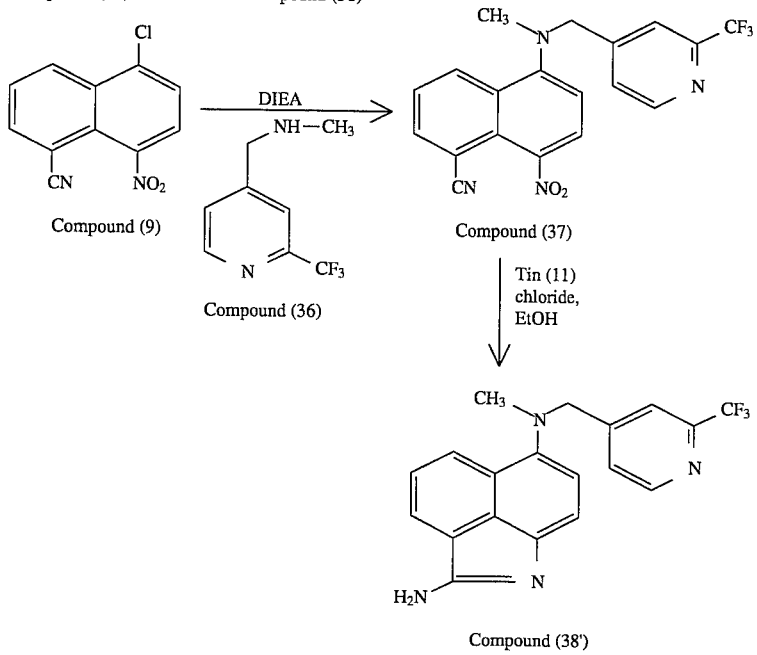

Preparation of (2-Trifluoromethylpyridin-4-yl)-methanol:

Compound (35) was prepared according to the procedure described in R. B. Katz et al., Synthetic Communications, 19, 1989, 317–325, giving, after flash chromatography on silica (eluting hexanes:ethyl acetate (2:1)), the product as an oil (12% yield).

IR (neat) 2872, 1615, 1431, 1329, 1184, 1138 cm$^{-1}$.

$^1$H NMR (CDCl$_3$) δ: 4.78 (s,2H), 7.46 (d,1H,J=5.0Hz), 7.67 (s,1H), 8.58 (d,1H,J=5.0Hz).

Anal. calc. for C$_7$H$_6$F$_3$NO.0.10H$_2$O: C, 46.98; H, 3.49; N, 7.83. Found: C, 46.90; H, 3.58; N, 7.76.

Preparation of Methyl-(2-trifluoromethyl-pyridin-4-ylmethyl)-amine:

To an ice-cold solution of 3.2 ml (43.84 mmol) of thionyl chloride was added dropwise a solution of 1.56 g (8.81 mmol) of alcohol (35) in 5 ml of CH$_2$Cl$_2$. After ten minutes at 0° C., the volatiles were removed, and the oily residue was dissolved in 10 ml of tetrahydrofuran. The resulting solution was added dropwise to 45 ml of 40 wt. % aqueous methylamine. After ten minutes at room temperature, the volatiles were removed, and the residue was diluted with ethyl acetate, washed with saturated NaHCO$_3$ solution, washed with saturated NaCl solution, and dried (MgSO$_4$). The solvent was removed under reduced pressure, producing 1.37 g (82% yield) of methyl-(2-trifluoromethyl-pyridin-4-ylmethyl)-amine (36) as an oil.

IR (neat) 3314, 2853 (broad), 1738, 1611, 1431, 1327, 1180, 1138 cm$^{-1}$.

$^1$H NMR (CDCl$_3$) δ: 2.47 (s,3H), 3.86 (s,2H), 7.47 (d,1H, J=4.9Hz), 7.69 (s,1H), 8.66 (d,1H,J=4.9Hz).

Anal. calc. for C$_8$H$_9$F$_3$N$_2$.0.20H$_2$O: C, 49.58; H, 4.89; N, 14.46. Found: C, 49.87; H, 4.79; N, 14.15.

Preparation of 5-{Methyl-(2-trifluoromethyl-pyridin-4-ylmethyl)amino}-8-nitro-naphthalene-1-carbonitrile:

Compound (37) was prepared in a manner analogous to that used to prepare compound (10), except using chloronaphthalene compound (9) and amine compound (36). The product was isolated by flash chromatography (eluting CH$_2$Cl$_2$) as a brittle yellow foam (38% yield), m.p. 104°–106° C.

IR (KBr) 2872, 2224, 1574, 1520, 1327, 1180, 1136, 1114 cm$^{-1}$.

$^1$H NMR (CDCl$_3$) δ: 2.94 (s,3H), 4.47 (s,2H), 7.21 (d,1H, J=8.3Hz), 7.55 (d,1H,J=5.0Hz), 7.68 (d,1H,J=7.3Hz), 7.71 (d,1H, J=7.3Hz), 7.74 (s,1H), 8.03 (d,1H,J=8.3Hz), 8.15 (d,1H,J=7.2Hz), 8.53 (d,1H,J=8.6Hz), 8.77 (d,1H,J=5.0Hz).

Anal. calc. for C$_{19}$H$_{13}$F$_3$N$_4$O$_2$: C, 59.07; H, 3.39; N, 14.50. Found: C, 59.31; H, 3.47; N, 14.27.

Preparation of N6-Methyl-N6-(2-trifluoromethyl-pyridin-4-ylmethyl)-benz[cd]indole-2,6-diamine:

Compound (38) was prepared in a manner analogous to that used to prepare compound (11), except using cyano-nitronaphthalene compound (37). Flash chromatography, eluting CH$_2$Cl$_2$:NH$_3$-saturated methanol (12:1), was used to isolate the product as a red solid (52% yield), m.p. 76°–80° C.

IR (KBr) 3154 (broad), 1644, 1613, 1530, 1464, 1427, 1327 cm$^{-1}$.

$^1$H NMR (CDCl$_3$) δ: 2.86 (s,3H), 4.44 (s,2H), 5.4 (brs, 2H), 6.89 (d,1H,J=6.9Hz), 7.03 (d,1H,J=7.5Hz), 7.59 (m,2H), 7.79 (s,1H), 7.82 (d,1H,J=7.0Hz), 8.05 (d,1H,J= 8.1Hz), 8.71 (d,1H,J=4.9Hz).

Anal. calc. for $C_{19}H_{16}F_3N_4$, M+H: 357.1327. Found: 357.1323.

Anal. calc. for $C_{19}H_{15}F_3N_4$: C, 64.04; H, 4.24; N, 15.72. Found: C, 64.12; H, 4.29; N, 15.67.

Example 5

N6-Methyl-N6-(2-methyl-pyridin-4-ylmethyl)-benz[cd]indole-2,6-diamine

The title compound (41) was prepared according to the following reaction scheme:

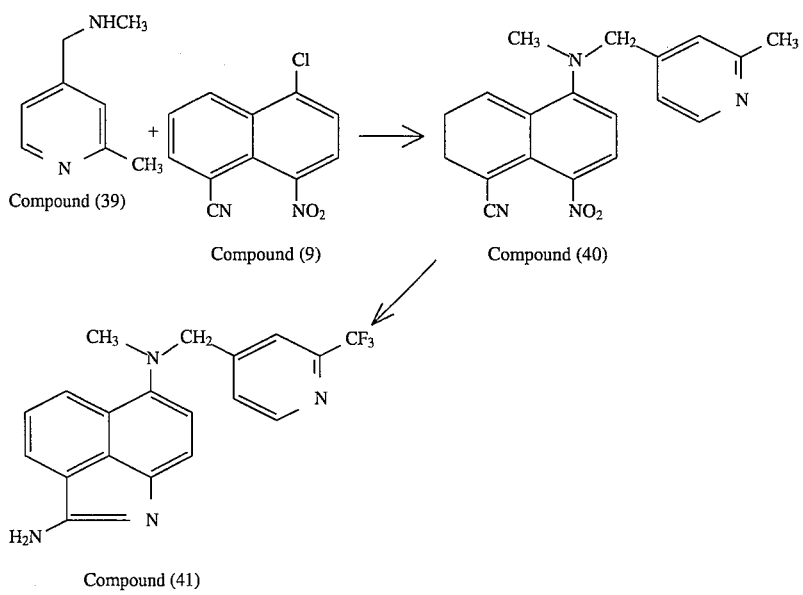

Preparation of Methyl-(2-methyl-pyridin-4-ylmethyl)-amine:

A stirred solution of 0.86 g (6.98 mmol) of 2-methyl-4-hydroxymethylpyridine (R. B. Katz et al., Synthetic Communications, 19, 1989, 317–325) in 48% aqueous HBr was heated at reflux for four days. The reaction mixture was cooled and added dropwise to 20 ml of 40% aqueous methylamine. The volatiles were removed under reduced pressure, and the residue was slurried in $CH_2Cl_2$ and then filtered. The filter cake was washed with $CH_2Cl_2$, EtOAc, $CH_3CN$, and 10% MeOH in $CH_3CN$. The filtrate was concentrated, and the residue was flash chromatographed on silica, eluting $CH_2Cl_2$:$NH_3$-saturated MeOH (9:1). Consequently, 0.65 g (68% yield) of methyl-(2-methyl-pyridin-4-ylmethyl)-amine (39) was obtained as a colorless liquid.

IR (neat) 3368 (broad), 1638, 1609, 1562, 1451, 1406 cm$^{-1}$.

$^1$H NMR (CDCl$_3$) δ: 2.45 (s,3H), 2.54 (s,3H), 3.73 (s,2H), 7.05 (d,1H,J=5.1Hz), 7.13 (s,1H), 8.42 (d,1H,J=5.1Hz).

Anal. calc. for $C_8H_{12}N_2.0.45H_2O$: C, 66.58; H, 9.01; N, 19.41. Found: C, 66.49; H, 8.73; N, 19.38.

Anal. calc. for $C_8H_{12}N_2$, M$^+$: 136.1000. Found: 136.0998.

Preparation of 5-{Methyl-(2-methyl-pyridin-4-ylmethyl)-amino}-8-nitro-naphthalene-1-carbonitrile:

Compound (40) was prepared in a manner analogous to that used to prepare compound (10), except chloronaphthalene compound (9) and amine compound (39) were used. Compound (40) was isolated as a yellow-brown solid (24% yield), m.p. 121°–123° C., by flash chromatography on silica, eluting $CH_2Cl_2$:EtOAc (1:1).

IR (KBr) 2226, 1641, 1572, 1449, 1414, 1335 cm$^{-1}$.

$^1$H NMR (CDCl$_3$) δ: 2.59 (s,3H), 2.93 (s,3H), 4.36 (s,2H), 7.16 (m,3H), 7.66 (t,1H,J=7.9Hz), 8.03 (d,1H,J=8.4Hz), 8.12 (d,1H,J=7.2Hz), 8.51 (m,2H).

Anal. calc. for $C_{19}H_{17}N_4O_2$, M$^+$:333.1351. Found: 333.1357.

Preparation of N6-Methyl-N6-(2-methyl-pyridin-4-ylmethyl)-benz[cd]indole-2,6-diamine:

Compound (41) was prepared in a manner analogous to that used to prepare compound (11), except cyano-nitronaphthalene compound (40) was used. Compound (41) was isolated as a dark-red solid (62% yield), m.p. 147°–150° C. (decomp.), by flash chromatography on silica, eluting $CH_2Cl_2$:$NH_3$-saturated MeOH (10:1).

IR (KBr) 3140 (broad), 1650, 1605, 1530, 1460, 1445 cm$^{-1}$.

$^1$H NMR (CDCl$_3$) δ: 2.58 (s,3H), 2.84 (s,3H), 2.86 (brs,2H), 4.36 (s,2H), 6.87 (d,1H,J=7.5Hz), 7.06 (d,1H,J=7.5Hz), 7.21 (d,1H,J=5.1Hz), 7.26 (s,1H), 7.59 (t,1H,J=7.9Hz), 7.81 (d,1H,J=7.0Hz), 8.10 (d,1H,J=8.1Hz), 8.49 (d,1H,J=5.1Hz).

Anal. calc. for $C_{19}H_{18}N_4$, M$^+$: 302.1531. Found: 302.1520.

Anal. calc. for $C_{19}H_{18}N_4.0.50H_2O.0.10(CH_3CH_2)_2O$: C, 73.09; H, 6.32; N, 17.58. Found: C, 72.87; H, 6.04; N, 17.18.

21

Example 6

5,N6-Dimethyl-N6-(2-methyl-pyridin-4-ylmethyl)-benz[cd]indole-2,6-diamine

The title compound (43) was prepared according to the following reaction scheme:

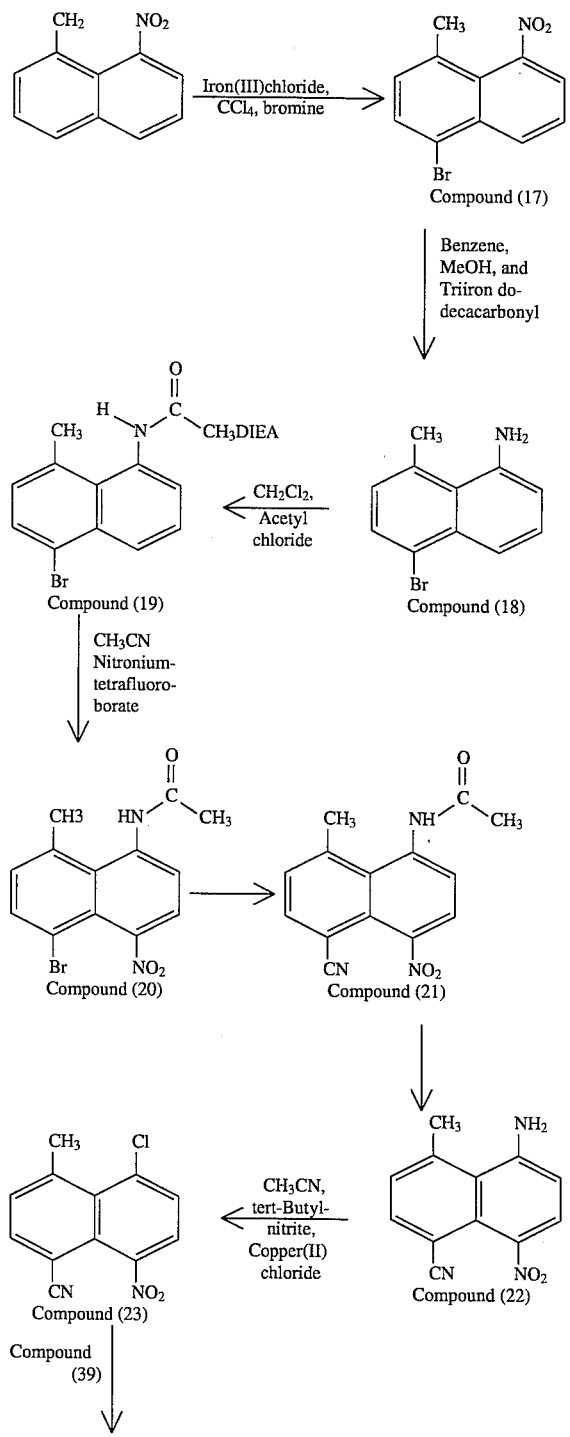

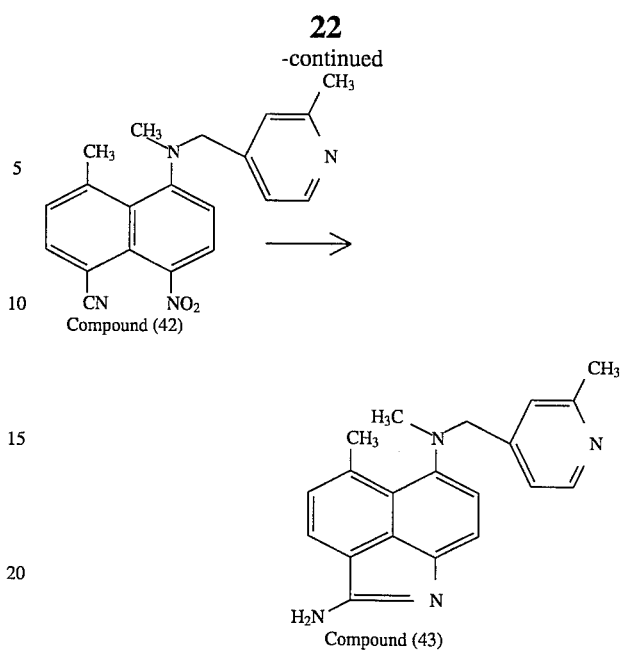

Preparation of 4-Bromo-1-methyl-8-nitro-naphthalene:

To a stirred solution of 10.60 g (56.32 mmol) of 8-methyl-1-nitro-naphthalene (V. Yesely, Chem. Zentralbl 1, 1930, 2134) and 0.45 g (2.77 mmol) of iron (III) chloride in 150 ml of $CCl_4$ heated to 60° C. was added dropwise 3.0 ml (58.23 mmol) of bromine. After one hour, the reaction mixture was poured into saturated $NaHCO_3$ solution, and the layers were separated. The aqueous layer was re-extracted with $CH_2Cl_2$. The combined organic layers were dried ($MgSO_4$) and the solvent was removed under reduced pressure. The crude residue was recrystallized from ethanol and the mother liquors were concentrated and then flash chromatographed on silica, eluting hexanes:ethyl acetate (12:1). The faster-moving 5-bromo isomer (17) was isolated as a brown solid, m p 101.5°–103.5° C. at an overall yield of 84%.

IR (KBr) 1524, 1443, 1360, 824 $cm^{-1}$.

$^1$H NMR ($CDCl_3$) δ: 2.51 (s,3H), 7.30 (d,1H,J=7.8Hz), 7.60 (t,1H,J=8.2Hz), 7.72 (d,1H,J=7.3Hz), 7.82 (d,1H,J=7.8Hz), 8.54 (d,1H,J=8.5Hz).

Anal. calc. for $C_{11}H_8BrNO_2.0.2H_2O$: C, 48.99; H, 3.14; Br, 29.63; N, 5.19. Found: C, 48.89; H, 3.09; Br, 29.90; N, 5.18.

The slower-moving 7-bromo isomer of compound (17) was isolated in a 5% yield.

Preparation of 4-Bromo-1-methyl-8-amino-naphthalene:

To a stirred solution of 12.54 g (47.13 mmol) of nitronaphthalene (17) in 210 ml of benzene and 10 ml of methanol was added 25.48 g (50.60 mmol) of tri-iron dodecacarbonyl (5% methanol). The reaction mixture was heated at reflux for five and a half hours, cooled to room temperature, and then filtered through Celite. The solvent was removed under reduced pressure to give 11.40 g of a purple oil, which was dissolved in 150 ml of $CH_2Cl_2$ and filtered through a pad of silica (1.5" length×4" width) to remove remaining iron residues. The $CH_2Cl_2$ was removed under reduced pressure. There was thus obtained 10.40 g (93% yield) of 4-bromo-1-methyl-8-amino-naphthalene (18), which was used in the next step without further purification.

$^1$H NMR (CDCl$_3$) δ: 2.96 (s,3H), 4.39 (brs,2H), 6.75 (d,1H,J=7.5Hz), 6.96 (d,1H,J=7.7Hz), 7.32 (t,1H,J=8.0Hz), 7.58 (d,1H,J=7.6Hz), 7.73 (d,1H,J=8.4Hz).

Preparation of N-(5-Bromo-8-methyl-naphthalen-1-yl)-acetamide:

To a stirred solution of 6.68 g (28.29 mmol) of amino-naphthalene compound (18) and 5.90 ml (33.87 mmol) of DIEA in 200 ml of CH$_2$Cl$_2$ at 0° C. was added dropwise 2.20 ml (30.94 mmol) of acetyl chloride. After 30 minutes at 0° C., a thick precipitate formed, which was filtered, washed with water and dried in vacuo. The filtrate was partitioned between 0.5N HCl and CH$_2$Cl$_2$. The organic layer was concentrated to about 20 ml, and the solid was collected by filtration and washed with cold CH$_2$Cl$_2$, producing overall 7.20 g (91% yield) of N-(5-bromo-8-methyl-naphthalen-1-yl)-acetamide (19) as a tan solid, m.p. 227°–229° C.

IR (KBr) 3231, 1644, 1535, 1366, 1294, 806 cm$^{-1}$.

$^1$H NMR (DMSO-D$_6$) δ: 2.08 (s,3H), 2.73 (s,3H), 7.21 (d,1H,J=7.7Hz), 7.42 (d,1H,J=7.1Hz), 7.63 (t,1H,J=8.4Hz), 7.76 (d,1H,J=7.7Hz), 8.14 (d,1H,J=8.4Hz), 9.91 (s,1H).

Anal. calc. for C$_{13}$H$_{12}$BrNO: C, 56.13; H, 4.35; Br, 28.73; N, 5.04. Found: C, 56.02; H, 4.38; Br, 28.62; N, 5.01.

Preparation of N-(5-Bromo-8-methyl-4-nitro-naphthalen-1-yl)-acetamides

To a cold (−5° C.) suspension of 4.45 g (16.00 mmol) of compound (19) in 25 ml acetonitrile was added dropwise a suspension of 2.60 g (16.64 mmol) of nitronium tetrafluoroborate in 5 ml of acetonitrile. After ten minutes, the homogenous, light-yellow reaction mixture was poured into water and extracted twice with ethyl acetate. The combined organic layers were washed with saturated NaCl solution and then dried over anhydrous MgSO$_4$. The solvent was then removed under reduced pressure, and the crude residue was recrystallized from methanol to give N-(5-bromo-8-methyl-4-nitro-naphthalen-1-yl)-acetamide (20) as a light-yellow solid, m.p. 216°–217° C. Another 0.80 g of compound (20) was obtained from the concentrated mother liquors after flash chromatography on silica, eluting hexanes:ethyl acetate (1:1). The overall yield was 2.00 g (39%).

IR (KBr) 3275, 1667, 1532, 1373, 1312, 1271 cm$^{-1}$.

$^1$H NMR (CDCl$_3$) δ: 2.29 (brs,3H), 2.87 (s,3H), 7.23 (d,1H,J=7.9Hz), 7.65 (brs,1H), 7.79 (m,3H).

Anal. calc. for C$_{13}$H$_{11}$BrN$_2$O$_3$: C, 48.32; H, 3.43; Br, 24.73; N, 8.67. Found: C, 48.42; H, 3.43; Br, 24.81; N, 8.58.

Preparation of N-(5-Cyano-8-methyl-4-nitro-naphthalen-1-yl)-acetamide:

Compound (21) was prepared in a manner analogous to the procedure described above used to prepare compound (7), except that bromo compound (20) was used. Compound (21) (89% yield), m.p. 208°–211° C., was isolated as a yellow solid by slurrying the crude product in hot CH$_2$Cl$_2$, cooling, and collecting the solid by filtration.

IR (KBr) 3283, 2226, 1661, 1535, 1510, 1352, 1269 cm$^{-1}$.

$^1$H NMR (DMSO-D$_6$) δ: 2.14 (s,3H), 2.88 (s,3H), 7.66 (d,1H, J=7.6Hz), 7.73 (d,1H,J=8.2Hz), 8.25 (d,1H,J=7.5Hz), 8.26 (d,1H,J=8.25Hz), 10.23 (s,1H).

Anal. calc. for C$_{14}$H$_{11}$N$_3$O$_3$: C, 62.45; H, 4.12; N, 15.61. Found: C, 62.32; H, 4.17; N, 15.47.

Preparation of 5-Amino-4-methyl-8-nitro-naphthalene-1-carbonitrile:

Compound (22) was prepared in a manner analogous to that described above for preparing compound (8), except that N-acetyl compound (21) was used. Compound (22) was isolated (81% yield) as a yellow solid, m.p. 174° C. (decomp.).

IR (KBr) 3507, 3353, 3252, 2224, 1644, 1582, 1493, 1474, 1296, 1271 cm$^{-1}$.

$^1$H NMR (DMSO-D$_6$) δ: 2.96 (s,3H), 6.81 (d,1H,J=8.9Hz), 7.07 (brs,2H), 7.40 (d,1H,J=7.6Hz), 8.05 (d,1H,J=7.5Hz), 8.09 (d,1H, J=8.9Hz).

Anal. calc. for C$_{12}$H$_9$N$_3$O$_2$: C, 63.43; H, 3.99; N, 18.49. Found: C, 63.50; H, 4.03; N, 18.45.

Preparation of 5-Chloro-4-methyl-8-nitro-naphthalene-1-carbonitrile:

A suspension of 1.31 g (5.77 mmol) of aniline compound (22) in 15 ml of acetonitrile was slowly added to a stirred solution of 1.15 ml (8.79 mmol) of tert-butylnitrite and 0.93 g (6.92 mmol) of copper (II) chloride in 50 ml of acetonitrile at room temperature. After forty-five minutes, the reaction mixture was poured into a 0.5N HCl solution and extracted twice with ethyl acetate. The combined organic layers were washed with saturated NaHCO$_3$ solution, washed with saturated NaCl solution, and then dried over anhydrous MgSO$_4$. The solvent was removed under reduced pressure, and the residue was refluxed in CH$_2$Cl$_2$, cooled and filtered. Thus, there was obtained 0.55 g of 5-chloro-4-methyl-8-nitro-naphthalene-1-carbonitrile (23). The mother liquors were concentrated and subjected to flash chromatography on silica, eluting hexanes:CH$_2$Cl$_2$ (1:1) to give another 0.62 g of compound (23). Overall, 1.17 g (82% yield) of compound (23) was produced as a tan solid, m.p. 179°–180° C.

IR (KBr) 3106, 2228, 1572, 1532, 1387, 1364, 1055 cm$^{-1}$.

$^1$H NMR (CDCl$_3$) δ: 3.18 (s,3H), 7.56 (d,1H,J=7.6Hz), 7.76 (d,1H,J=8.2Hz), 7.84 (d,1H,J=8.2Hz), 7.99 (d,1H,J=7.6Hz).

Anal. calc. for C$_{12}$H$_7$ClN$_2$O$_2$: C, 58.43; H, 2.86; Cl, 14.37; N, 11.36. Found: C, 58.50; H, 2.86; Cl, 14.43; N, 11.33.

Preparation of 4-Methyl-5-{methyl-(2-methyl-pyridin-4-ylmethyl)-amino}-8-nitro-naphthalene-1-carbonitrile:

Compound (42) was prepared in a manner analogous to that used to prepare compound (10), except that chloronaphthalene compound (23) and amine compound (39) were employed. Compound (42) was isolated as a yellow solid (4% yield) by flash chromatography on silica, eluting CH$_2$Cl$_2$: EtOAc (1:1).

$^1$H NMR (CDCl$_3$) δ: 2.52 (s,3H), 2.73 (s,3H), 3.04 (s,3H), 4.16 and 4.34 (AB system, 2H,J=14.2Hz), 6.78 (d,1H,J=5.1Hz), 6.85 (s,1H), 7.05 (d,1H,J=8.5Hz), 7.45 (d,1H,J=7.7Hz), 7.94 (d,1H, J=8.4Hz), 7.96 (d,1H,J=7.5Hz), 8.43 (d,1H,J=5.1Hz).

Anal. calc for C$_{20}$H$_{18}$N$_4$O$_2$, M$^+$: 346.1430. Found: 346.1424.

Preparation of 5,N6-Dimethyl-N6-(2-methyl-pyridin-4-ylmethyl)-benz[cd]indole-2,6-diamine:

Compound (43) was prepared in a manner analogous to that used to prepare compound (11), except that cyano-nitronaphthalene compound (42) was employed. Compound (43) was isolated as an orange-brown solid (50% yield), m.p. 180° C. (decomp.), by flash chromatography, eluting CH$_2$Cl$_2$:NH$_3$-saturated MeOH (10:1).

IR (thin film) 3173, 1651, 1607, 1537, 1462, 1447, 1404 cm$^{-1}$.

$^1$H NMR (CD$_3$OD) δ: 2.46 (s,3H), 2.71 (s,3H), 3.16 (s,3H), 4.17 and 4.39 (AB system, 2H,J=14.4Hz), 7.03 (d,1H,J=7.5Hz), 7.13 (d,1H,J=7.6Hz), 7.21 (d,1H,J=4.8Hz), 7.26 (s,1H), 7.51 (d,1H, J=7.3Hz), 7.99 (d,1H,J=7.3Hz), 8.27 (d,1H,J=5.2Hz).

Anal. calc. for C$_{20}$H$_{21}$N$_4$, M+H: 317.1766. Found: 317.1780.

Example 7

5,N6-Dimethyl-N6-pyridin-4-ylmethyl-benz[cd]indole-2,6-diamine

The title compound (46) was prepared according to the following reaction scheme:

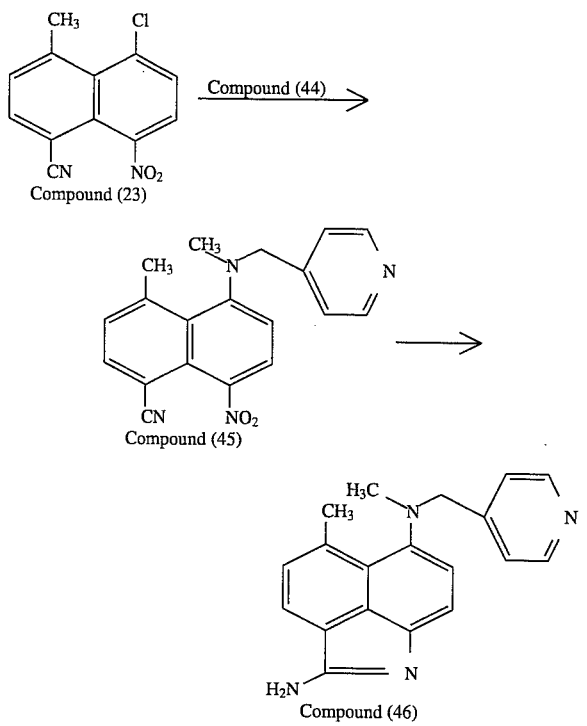

Preparation of 4-Methyl-5-(methyl-pyridin-4-ylmethyl-amino)-8-nitro-naphthalene-1-carbonitrile:

Compound (45) was prepared in a manner analogous to that used to prepare compound (10) as described above, except that chloronaphthalene compound (23) and amine compound (44), prepared as described above, were employed. Compound (45) was isolated as a yellow solid (8% yield), m.p. 157°–158° C., by flash chromatography on silica, eluting $CH_2Cl_2$:EtOAc (1:1).

IR (KBr) 2928, 2222, 1597, 1568, 1512, 1329, 1310 cm$^{-1}$.

$^1$H NMR (CDCl$_3$) δ: 2.73 (s,3H), 3.05 (s,3H), 4.20 and 4.39 (AB system, 2H,J=14.2Hz), 6.99 (d,2H,J=6.0Hz), 7.05 (d,1H,J=8.4Hz), 7.46 (d,1H,J=7.5Hz), 7.94 (d,1H,J=8.3Hz), 7.96 (d,1H,J=6.5Hz), 8.56 (d,2H,J=6.0Hz).

Anal. calc. for $C_{19}H_{17}N_4O_2$, M+H: 333.1352. Found: 333.1350.

Preparation of 5,N6-Dimethyl-N6-pyridin-4-ylmethyl-benz[cd]indole- 2,6-diamine:

Compound (46) was prepared in a manner analogous to that used to prepare compound (11), except that cyano-nitronaphthalene compound (45) was employed. The product was isolated (63% yield) by flash chromatography, eluting CHCl$_3$: MeOH:HOAc (85:10:5). The appropriate fractions were concentrated, dissolved in EtOAc, washed with saturated NaHCO$_3$ solution and dried (MgSO$_4$), and the solvent was removed under reduced pressure to give the free base (46) as a rust-colored solid, m.p. 144°–146° C.

IR (KBr) 3202 (broad), 1657, 1605, 1532, 1462, 1447, 1418 cm$^{-1}$.

$^1$H NMR (CDCl$_3$) δ: 2.73 (s,3H), 3.18 (s,3H), 4.00 (brs,2H), 4.15 and 4.44 (AB system, 2H,J=14.2Hz), 7.12 (AB system, 2H, J=7.3Hz), 7.30 (d,2H,J=5.2Hz), 7.47 (d,1H,J=7.0Hz), 7.75 (d,1H,J=6.9Hz), 8.60 (d,2H,J=5.2Hz).

Anal. calc. for $C_{19}H_{19}N_4$, M+H: 303.1610. Found: 303.1622.

Example 8

The following compound is synthesized in a manner similar to the syntheses used to prepare the above examples:

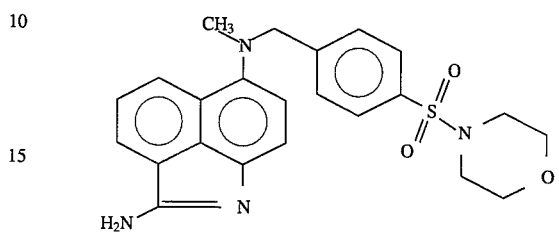

The above examples illustrate various features of the invention, and are not intended to limit the spirit or scope of the invention defined in the appended claims. Other embodiments and modifications will be apparent to those skilled in the art.

What is claimed is:

1. A compound of the Formula B:

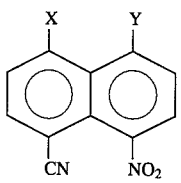

(B)

wherein:

X is a hydrogen atom or a $C_{1-6}$ alkyl group; and

Y is a group of the formula

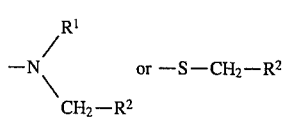

where $R^1$ is a hydrogen atom or a substituted or unsubstituted $C_{1-6}$ alkyl group having from 0 to 3 carbon atoms replaced by a hetero atom, and $R^2$ is an aryl or heteroaryl ring that is unsubstituted or substituted with an electron-donating or electron-withdrawing moiety.

2. A compound of claim 1, wherein Y is said group of the formula

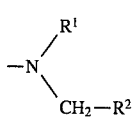

where:

$R^1$ is a hydrogen atom or a methyl group; and $R^2$ is a phenyl, naphthyl or heteroaryl ring that is unsubstituted or substituted with an electron-donating or electron-withdrawing moiety.

3. A compound of claim 2, wherein X is a hydrogen atom or a methyl group.

* * * * *